United States Patent
Tetta et al.

(10) Patent No.: US 11,453,863 B2
(45) Date of Patent: Sep. 27, 2022

(54) PANCREATIC ISLET-LIKE CELL STRUCTURES AND A METHOD OF PREPARING THEREOF

(71) Applicant: Fresenius Medical Care Deutschland GmbH, Bad Homburg (DE)

(72) Inventors: Ciro Tetta, Mirandola (IT); Giovanni Camussi, Turin (IT); Sara Giunti, Turin (IT); Victor Manuel Navarro Tableros, Turin (IT)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 607 days.

(21) Appl. No.: 16/203,869

(22) Filed: Nov. 29, 2018

(65) Prior Publication Data

US 2019/0119648 A1  Apr. 25, 2019

Related U.S. Application Data

(62) Division of application No. 15/103,317, filed as application No. PCT/EP2014/077976 on Dec. 16, 2014, now Pat. No. 10,174,286.

(30) Foreign Application Priority Data

Dec. 16, 2013 (EP) .................................. 13197368

(51) Int. Cl.
*C12N 5/071* (2010.01)
*A61L 27/38* (2006.01)

(52) U.S. Cl.
CPC ........ *C12N 5/0677* (2013.01); *A61L 27/3804* (2013.01); *A61L 2430/00* (2013.01); *C12N 2501/00* (2013.01); *C12N 2501/998* (2013.01); *C12N 2506/14* (2013.01); *C12N 2533/32* (2013.01)

(58) Field of Classification Search
CPC .................................................. C12N 5/0677
See application file for complete search history.

(56) References Cited

U.S. PATENT DOCUMENTS

| | | |
|---|---|---|
| 2005/0074876 A1 | 4/2005 | Strick-Marchand et al. |
| 2006/0246418 A1 | 11/2006 | Montminy |
| 2008/0148074 A1 | 6/2008 | Gorfien |
| 2009/0053758 A1 | 2/2009 | Kubota et al. |
| 2010/0093090 A1 | 4/2010 | Deng et al. |

FOREIGN PATENT DOCUMENTS

| | | |
|---|---|---|
| CN | 102517248 | 6/2012 |
| EP | 1394263 | 3/2004 |
| WO | WO 00/03001 | 1/2000 |
| WO | WO 00/43498 | 7/2000 |
| WO | WO 03/033697 | 4/2003 |
| WO | WO 03/078588 | 9/2003 |
| WO | WO 2006/126219 | 11/2006 |
| WO | WO 2006/126236 | 11/2006 |
| WO | WO 2009/090424 | 7/2009 |

OTHER PUBLICATIONS

Chandra et al., Islet-like cell aggregates generated from human adipose tissue derived stem cells ameliorate experimental diabetes in mice. PLoS One, vol. 6, No. 6 (2011) e20615. (Year: 2011).*
Chandra et al. Islet-like cell aggregates generated from human adipose tissue derived stem cells ameliorate experimental diabetes in mice, PLOS One, vol. 6, issue 6, Jun. 2011, pp. 1-12.
Kroon et al. Pancreatic endoderm derived from human embryonic stem cells generates glucose-responsive insuline-secreting cells in vivo. Nature Biotechnology, vol. 26, No. 4, Apr. 2008, pp. 443-452.
Rezania et al. Maturation of human embryonic stem cell-derived pancreatic progenitors into functional islets capable of treating pre-existing diabetes in mice. Diabetes, vol. 61, Aug. 2012, pp. 2016-2029.
Bose et al. Human embryonic stem cell differentiation into insulin secreting β-cells for diabetes. Cell Biology International, (2012) 36, 1013-1020.
Buang et al. In vitro generation of functional insulin-producing cells from lipoaspirated human adipose tissue-derived stem cells. Archives of Medical Research 43 (2012) 83-88.
Milanesi et al. Differentiation of nestin-positive cells derived from bone marrow into pancreatic endocrine and ductal cells in vitro. Journal of Endocrinology (2011) 209, 193-201.
Carnevale et al. In vitro differentiation into insulin-producing β-cells of stem cells isolated from human amniotic fluid and dental pulp. Digestive and Liver Disease 45 (2013) 669-676.
Prabakar et al. Generation of glucose-responsive, insuline-producing cells from human umbilical cord blood-derived mesenchynal stem cells. Cell Transplantation, vol. 21, pp. 1321-1339, 2012.
Ramiya et al. Reversal of insulin-dependent diabetes using islets generated in vitro from pancreatic stem cells. Nature Medicine, vol. 6, No. 3, Mar. 1, 2000, pp. 278-282.
Herrera et al. Isolation and characterization of a stem cell population from adult human liver. Stem Cells, vol. 24, No. 12, Jan. 1, 2006, pp. 2840-2850.
Jamal et al. Morphogenetic plasticity of adult human pancreatic islets of Langerhans. Cell Death and Differentiation, vol. 12, No. 7, Apr. 8, 2005, pp. 702-712.
Yang et al. In Vitro Transdifferentiation of adult hepatic stem cells into pancreatic endocrine cells. Blood. vol. 98, No. 11, part 01, Nov. 16, 2001, pp. 548A.
Lumelsky et al. Differentiation of embryonic stem cells to insulin-secreting structures similar to pancreatic islets. Science vol. 292, No. 5520, May 18, 2001, pp. 1389-1394.

(Continued)

*Primary Examiner* — Kara D Johnson
(74) *Attorney, Agent, or Firm* — Jacobson Holman PLLC

(57) ABSTRACT

The invention relates to a method of preparing pancreatic islet-like cell structures characterized by a unique combination of morphological and functional features which make them particularly suitable for use in both clinical and drug screening application, as well as to the pancreatic islet-like cell structures obtained therefrom.

3 Claims, 9 Drawing Sheets

(56) References Cited

OTHER PUBLICATIONS

Figure 2:
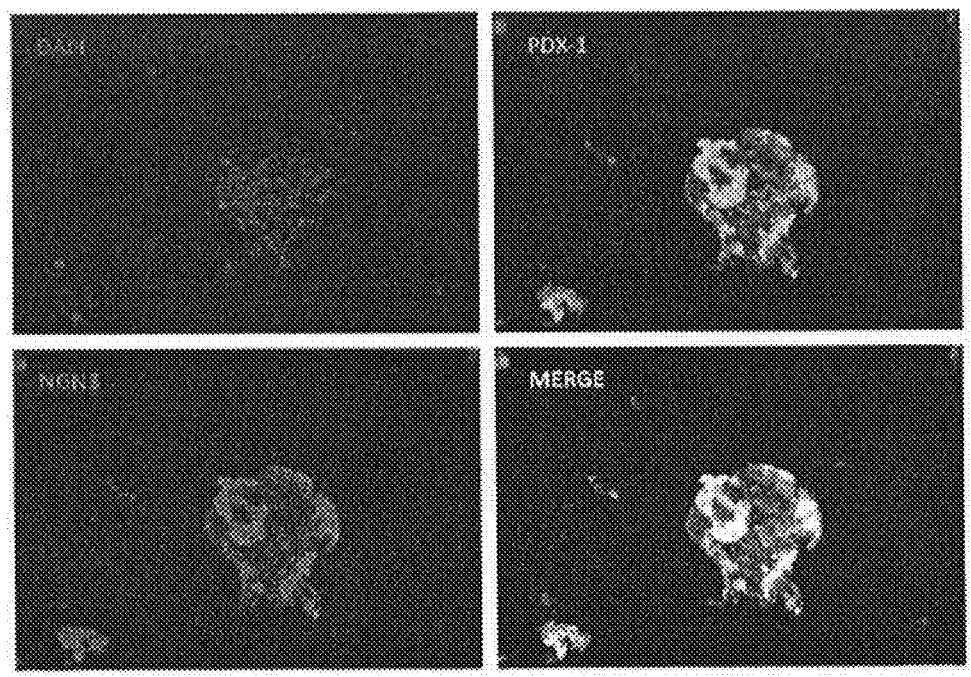

Wen et al. A spheroid-based 3D culture model for pancreatic cancer drug testing, using the acid phosphatase assay. Brazilian Journal of Medical and Biological Research, vol. 46, No. 7, Aug. 1, 2013, pp. 634-642.

Chun et al. Adhesive growth of pancreatic islet cells on a polyglycolic acid fibrous scaffold. Transplantation Proceedings, vol. 40, No. 5, Jun. 1, 2008, pp. 1658-1663.

Duan et al. Improvement in the methods for separation and culture of neural stem cells in striatum of embryonic rats. Chines J. Clin. vol. 9, No. 26, Jul. 14, 2005, pp. 92-93.

Fischer et al. In vitro cytotoxicity testing of polycations: influence of polymer structure on cell viability and hemolysis. Biomaterial, vol. 24, No. 7, Mar. 2003, pp. 1121-1131.

Yang et al. In vitro trans-differentiation of adult hepatic stem cells into pancreatic endocrine hormone-producing cells. PNAS USA, 99, 8078-8083, Jun. 11, 2002.

Malhi et al. Isolation of Human Progenitor Liver Epithelial Cells with Extensive Replication Capacity and Differentiation into Mature Hepatocytes. Journal of Cell Science, vol. 115, No. 13, pp. 2679-2688, Jul. 1, 2002.

Suzuki et al. Flow Cytometric Separation and Enrichment of Hepatic Progenitor Cells in the Developing Mouse Liver. Hepatology, vol. 32, No. 6, pp. 1230-1239, Dec. 6, 2000.

Schwartz et al. Multipotent Adult Progenitor Cells from Bone Marrow Differentials into Functional Hepatocyte-like Cells. Journal of Clinical Investigation, vol. 109, No. 10, pp. 1291-1302, May 2002.

Suzuki et al. Clonal Identification and Characterization of Self-Renewing Pluripotent Stem Cells in the Developing Liver, Journal of Cell Biology, vol. 156, No. 1, pp. 173-184, Jan. 7, 2002.

Forbes et al. Hepatic Stem Cells, Journal of Pathology, vol. 197, No. 4, pp. 510-518, May 30, 2002.

Petersen et al. Hepatic Oval Cells Express Stem Cell Markers Thy-1 in the Rat, Heptalogy, vol. 27, n. 2, pp. 433-445, Feb. 1998.

Petersen et al. Mouse A6-Positive Hepatic Oval Cells Also Express Several Hematopoietic Stem Cell Markers, Heptalogy, vol. 37, No. 3, pp. 632-640, Mar. 2003.

Mitaka et al. Reconstruction of Hepatic Organoid by Hepatic Stem Cells, Journal of HBP Surger, pp. 697-703, 2002.

Hillen et al. Control of Expression of the Tn10-encoded Tetracycline Resistance Genes, Journal of Mol.Biology, vol. 169, pp. 707-721, 1983.

Hillen et al. Analysis of tet Operator-TET Repressor Complexes by Thermal Denaturation Studies, Nucleic Acid Research, vol. 10, No. 19, pp. 6085-6097, 1982.

Hillen et al. Mechanisms Underlying Expression of Tn10 encoded Tetracycline Resistance, Microbioloy, pp. 345-369, 1994.

\* cited by examiner

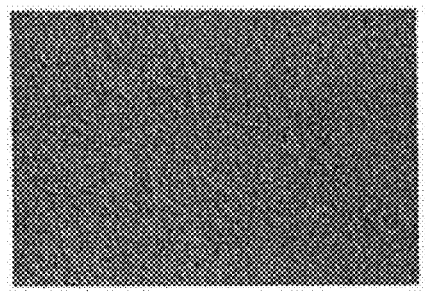 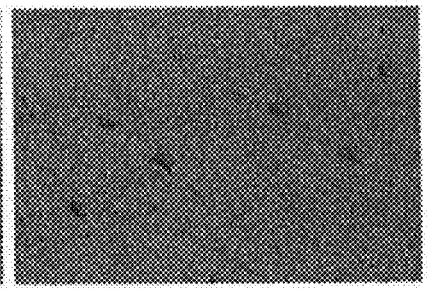
FIG. 1A  FIG. 1B
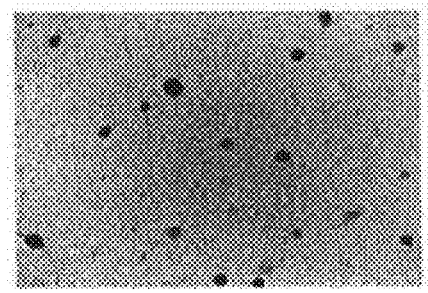 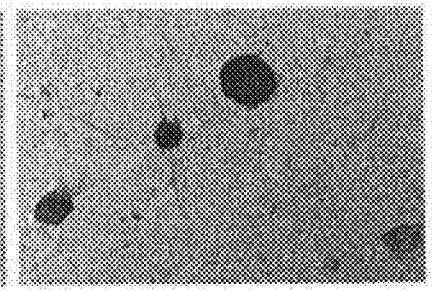
FIG. 1C  FIG. 1D
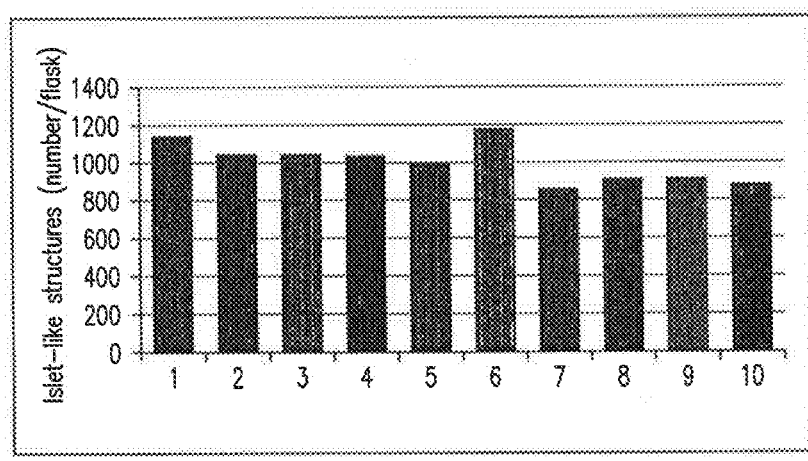 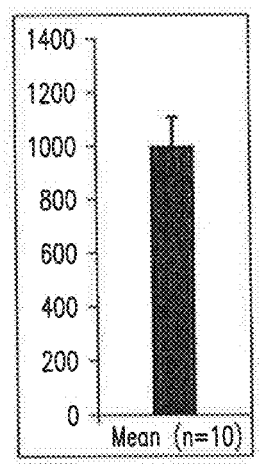
FIG. 1E  FIG. 1F

PANCREATIC ISLET-LIKE CELL STRUCTURES AND A METHOD OF PREPARING THEREOF

The present invention relates to the field stem cell differentiation. In particular, the present invention relates to a method for differentiating a stem cell into a pancreatic islet-like cell structure and to the pancreatic islet-like cell structure obtained therefrom.

Type 1 diabetes is a disease with a huge socio-economic impact that, if untreated, leads to death. It is caused by autoimmune destruction of pancreatic insulin producing cells (β-cells) and associated with the development of debilitating microvascular and macrovascular complications.

Both pancreas transplantation and islets transplantation have been shown to restore islets function and potentially reduce long-term diabetic complications, but are limited by both donor shortage and the need for immunosuppression. In this context, stem cells represent a promising source for the generation of insulin-producing cells, as they may have properties that allow to satisfy the requirements for the cure of type 1 diabetes mellitus (T1DM). Firstly, they may allow both to restore β-cell function and prevent recurrence of autoimmunity, without the need of using immunosuppressive therapy. Secondly, due to their potentially unlimited capacity for self-renewal, they could be broadly used.

In vitro methods to generate, under specific culture conditions, islets-like structures from human embryonic stem cells (Kroon E et al. Nat Biotechnol. 2008; 26(4): 443-52; Rezania A et al. Diabetes. 2012; 61(8): 2016-29; Bose B et al. Cell Biol Int. 2012; 36(11): 1013-20), human adipose tissue-derived stem cells (Mohamad Buang M L et al. Arch Med Res. 2012; 43(1): 83-8; Chandra V et al. PLoS One. 2011; 6(6):e20615), nestin-positive cells derived from bone marrow (Milanesi A et al. J Endocrinol. 2011; 209(2); 193-201), stem cells isolated from human amniotic fluid and dental pulp (Carnevale G et al. Dig Liver Dis. 2013; 45(8): 669-76), and human umbilical cord blood-derived mesenchymal stem cells (Prabakar K R et al. Cell Transplant. 2012; 21(6): 1321-39) are disclosed in the prior art.

However, islets-like structures derived in vitro from human embryonic stem cells were found to be immature, thus requiring a further in vivo 3-to-4 month differentiation period in order to become mature functional islets (Kroon E et al. Nat Biotechnol. 2008; 26(4): 443-52; Rezania A et al. Diabetes. 2012; 61(8): 2016-29). Furthermore, one study reporting 3D in vitro generation of insulin secreting cells from human embryonic stem cells, while showing a stable trend to a decrease in glycaemia from 300 mg/dl to 200 mg/dl, did not demonstrate, with the exception of insulin, protein expression of other hormones usually produced within the pancreatic islets (glucagon, pancreatic polypeptide (PP), somatostatin and ghrelin) (Bose B et al. Cell Biol Int. 2012; 36(11): 1013-20).

Insulin-producing cells generated in vitro from human adipose tissue-derived stem cells (Mohamad Buang M L et al. Arch Med Res. 2012; 43(1): 83-8; Chandra V et al. PLoS One. 2011; 6(6):e20615), nestin-positive cells derived from bone marrow (Milanesi A et al. J Endocrinol. 2011; 209(2); 193-201), stem cells isolated from human amniotic fluid and dental pulp (Carnevale G et al. Dig Liver Dis. 2013; 45(8): 669-76) were shown to release human insulin in response to glucose stimulation in vitro. However, expression of glucagon, PP and ghrelin was not demonstrated.

Insulin-producing cells generated from human umbilical cord blood-derived mesenchymal stem cells (CB-MSC) were shown to express insulin, C-peptide, glucagon and pancreatic polypeptide and to release C-peptide in response to glucose stimulation in vitro. However, the ability of such cells to reduce blood glucose in experimental diabetes was not demonstrated, as the authors only showed in vivo differentiation of engrafted CB-MSC-derived pancreatic endodermal cells into functional endocrine cells with detection of low levels of C-peptide following glucose challenge 60 days after the implantation (Prabakar K R et al. Cell Transplant. 2012; 21(6): 1321-39).

Methods of differentiation of human liver stem cells (HLSCs) into pancreatic islet cells are disclosed in Herrera M B et al. Stem Cells. 2006; 24(12):2840-50 and in International patent application WO 2006/126236.

In Herrera M B et al. Stem Cells. 2006; 24(12):2840-50, HLSCs were shown to change their elongated morphology into small spheroid cell clusters, morphologically resembling pancreatic islets, when cultured in DMEM with high glucose content (23 mM) for a month followed by 5-7 days of culture in the presence of 10 mM nicotinamide. Such spheroid cell clusters were positively stained for human insulin and Glut2 and became positively stained with the zinc-chelating agent dithizone, which is specific for insulin-containing granules, suggesting the differentiation of HLSCs into islet-like structures. Despite such exciting results, the differentiation protocol was limited by a low efficiency, particularly referring to both the quantity of the generated structures and the time required for generating them. Furthermore, even after extensive culturing the structures did not quite grow to a size and morphology closely resembling human pancreatic structures.

In order to overcome the drawbacks of the prior art, the present inventors have provided a new method of preparing a spheroid pancreatic islet-like cell structure, which is defined in the appended claims. The content of the claims forms an integral part of the description.

Compared to the prior art, not only the method according to the present invention is simpler, faster and more efficient, but it also results in structures which more closely resemble natural human pancreatic islet structures both in size and morphology. It results in the generation of a higher number of pancreatic islet-like cell structures which, advantageously, have a diameter comparable to the naturally-occurring human pancreatic islets and which express, at the protein level, all of the hormones which are usually produced by human pancreatic islets (i.e. insulin, glucagon, PP, somatostatin and ghrelin). Moreover, following implant under the kidney capsule of streptozotocin-induced diabetic SCID mice, the pancreatic islet-like cell structures obtainable by the method of the present invention are capable of reducing blood glucose levels significantly early (within 13 days), with a concomitant increase in human C-peptide. To the inventors' knowledge, such strong similarity of structural features to natural human pancreatic islet structures render unique the pancreatic islet-like cell structures generated with the method of the invention. Indeed, no previous studies have shown such a combination of in vitro and in vivo features in islet-like structures derived from a single isolated stem cell type. Due to their features, the pancreatic islet-like cell structures obtainable by the method of the present invention are particularly suitable for use in various applications, such as basic research, drug screening and regenerative medicine.

Thus, in a first aspect, the invention provides a method of preparing an artificially grown spheroid pancreatic islet-like cell structure, which comprises the step of culturing an isolated adult stem cell in a first differentiation liquid cell culture medium which comprises a poly-cationic substance.

Actually, the inventors surprisingly found that isolated adult stem cells, when cultured in a liquid cell culture medium in the presence of a poly-cationic substance, quite early (i.e. after about 2 to 4 days) aggregate and differentiate into spheroid pancreatic islet-like cell structures, which closely resemble naturally-occurring pancreatic islet cell structures both in size and morphology, and which are capable of expressing the hormones which are usually produced by human pancreatic islets (i.e. insulin, glucagon, PP, somatostatin and ghrelin).

The adult stem cell used in the method of the invention is preferably an adult mammalian stem cell. Therefore, any liquid cell culture medium capable of sustaining the growth of mammalian cells is suitable for use in the method of the invention. In a preferred embodiment, the liquid cell culture medium is a serum-enriched cell culture medium. Serum-enriched DMEM or RPMI are mentioned as non-limiting examples. Serum concentration in the cell culture medium is preferably comprised within the range of from 5 to 20%. Preferably, the liquid cell culture medium also comprises one or more carbon sources, such as for example glucose and glutamine. Preferred glucose concentrations are within the range of 6-25 mM. Preferred glutamine concentrations are within the range of 0.5-3 mM.

Within the context of the present description, the expression "adult stem cell" is intended to mean a stem cell that is isolated from an adult tissue, in contrast with an "embryonic stem cell" which is isolated from the inner cell mass of a blastocyst. Adult stem cells are also known as "somatic stem cells".

Any poly-cationic substance which is capable of promoting adult stem cell aggregation and differentiation into pancreatic islet cells at a given concentration and which, at that concentration is non-cytotoxic to cells, may be used in the method of the present invention. Illustrative, non-limiting examples of poly-cationic substances suitable for use in the method of the invention are poly-lysine and protamine.

Protamine, which is the preferred poly-cationic substance because it is suitable for clinical applications, is preferably added to the medium in the form of a soluble salt, such as for example protamine sulfate or protamine hydrochloride, at a concentration which preferably ranges between 5 and 20 mM.

In another preferred embodiment, the method of the invention further comprises the step of replacing the first differentiation liquid cell culture medium with a second differentiation liquid cell culture medium not comprising a poly-cationic substance and culturing the cells in said second medium. Any liquid cell culture medium capable of sustaining the growth of mammalian cells is suitable for use as the second differentiation liquid cell culture medium. According to a preferred embodiment, the same liquid cell culture medium which was used in the first step shall also be employed in the second step, except that it does not contain the poly-cationic substance. The aim of this step is to obtain complete maturation of the pancreatic islet-like cell structures formed during the first step as well as their increase both in cell number and in structure number. Cultivation in the second differentiation liquid cell culture medium is preferably carried out for a period of time of at least 2 days, more preferably for at least 10 days, even more preferably for about 10 to 14 days.

As mentioned above, the presence of a poly-cationic substance in the first differentiation liquid cell culture medium is the key element of the invention, in that it accelerates the formation of spheroid cell clusters resembling islets-like structures which closely resemble naturally occurring human pancreatic islet structures.

Figure 11:
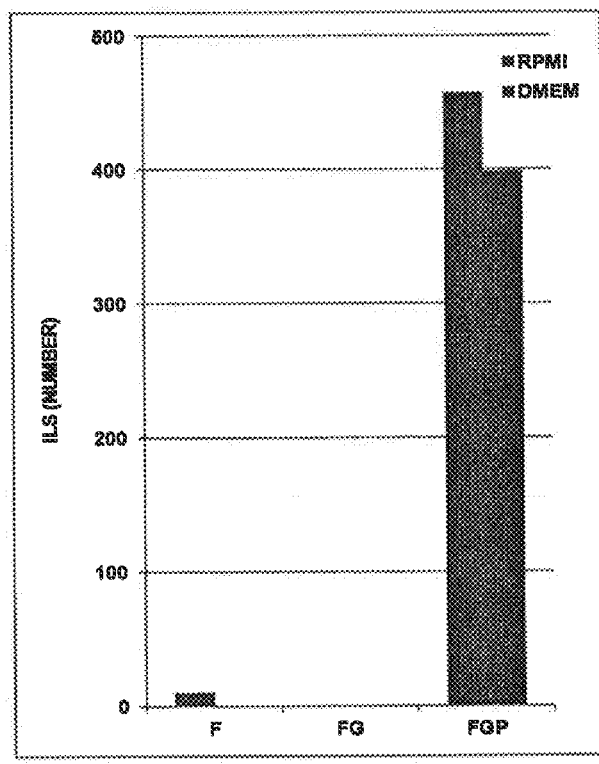

Indeed, as illustrated in the examples which follow, HLSCs exposure to either DMEM or RPMI-based differentiation media (see Tables 2 and 3 below), both in the presence and in the absence of glucose, did not result in islet-like structures formation after a culture period of 4 days. By contrast, the addition of protamine to either a DMEM or RPMI-based medium, both in the presence and in the absence of glucose, resulted in islet-like structures formation after a culture period of 4 days (FIG. 11). Diameter of the structures derived from HLSCs is comparable to that reported for human pancreatic islets (Chandra V et al. PLoS One. 2011; 6(6):e20615) and mostly comprised between 50 and 150 um, with an average islets volume of 109±19 uM (mean±SD) (FIG. 12).

Figure 13A:
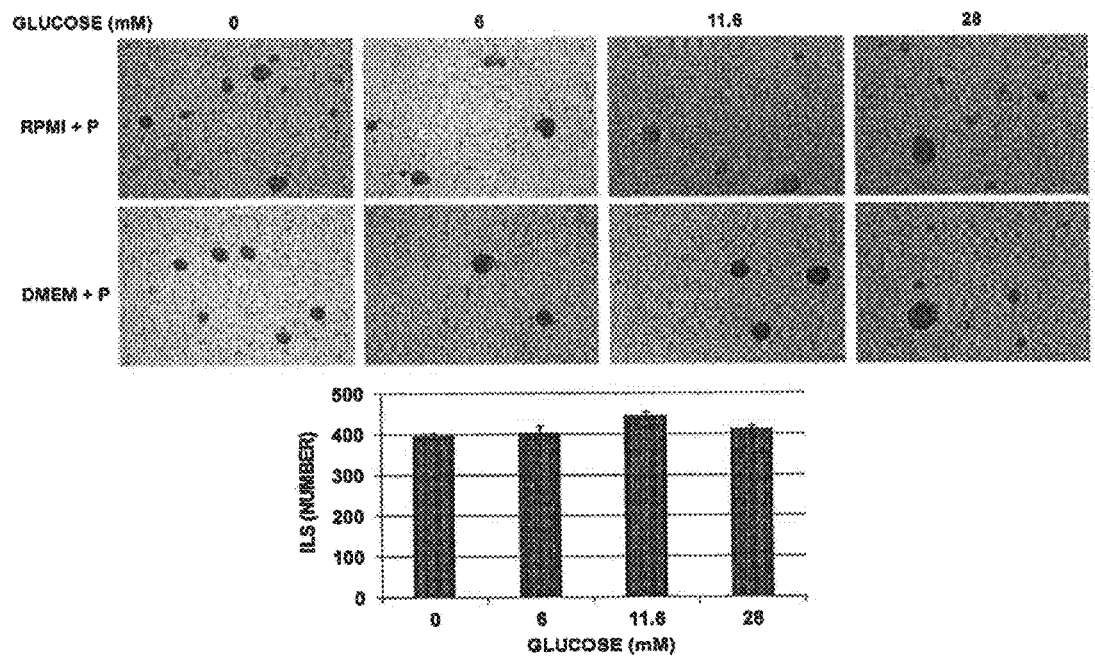
Figure 13B:
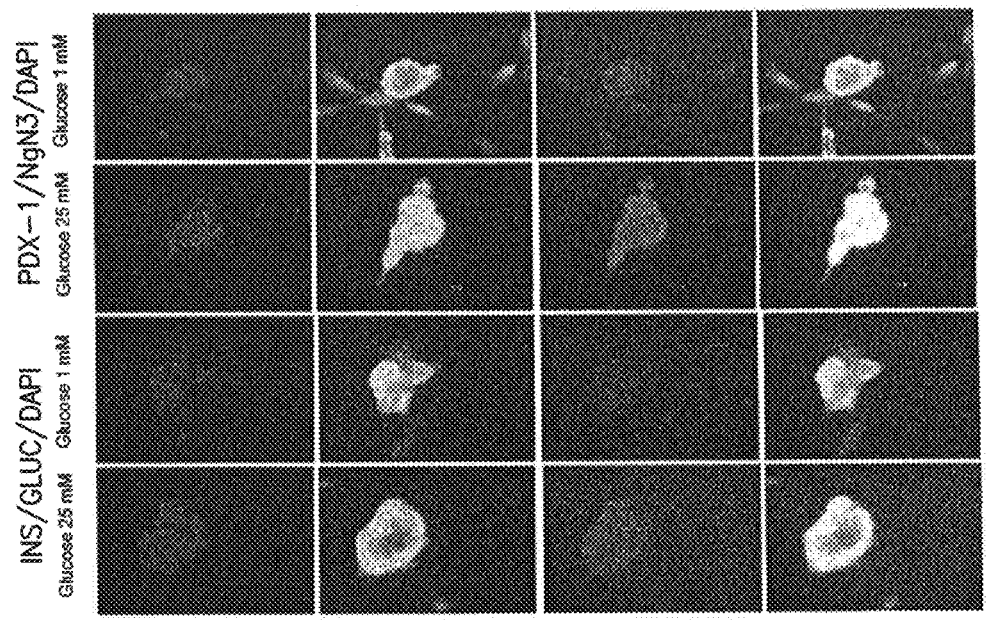

In contrast, glucose did not affect islet-like structures formation (FIG. 13A), but it plays a key role in both inducing endocrine specification (NgN3 expression) and increasing both insulin and glucagon expression within the structures (FIG. 13B).

According to another preferred embodiment of the invention, the adult stem cell which is differentiated into pancreatic islet-like cell structures is an adult human liver stem cell (HLSC). A preferred human liver stem cell is the human non-oval liver stem cell (HLSC) expressing both mesenchymal and embryonic stem cell markers disclosed in WO 2006/126219. This cell line is in particular characterised in that it is a non-oval human liver pluripotent progenitor cell line which is isolated from adult tissue, which expresses hepatic cell markers and which has multipotent differentiation abilities and regenerative properties. More in particular, this cell line is capable of differentiating into mature liver cells, insulin producing cells, osteogenic cells and epithelial cells. According to a preferred embodiment, it expresses one or more markers selected from the group comprising albumin, α-fetoprotein, CK18, CD44, CD29, CD73, CD146, CD105, CD90 and any combination thereof, and it does not express markers selected from the group comprising CD133, CD117, CK19, CD34, cytochrome P450.

The human non-oval liver pluripotent progenitor/stem cells disclosed in WO 2006/126236 were shown to undergo differentiation into a variety of tissue cell types (namely, mature liver cells, epithelial cells, insulin-producing cells and osteogenic cells) and to exert organ regenerating effects. Such cells are derived from a non-oval human liver pluripotent progenitor cell line which expresses hepatic cell markers. Such cells are isolated by a method comprising the steps of:
  (i) culturing adult liver-derived human mature hepatocytes in a cell culture medium until death of mature hepatocytes and selection of a population of surviving cells having epithelioid morphology;
  (ii) expanding the population of surviving cells having epithelioid morphology by culturing in a serum-containing, glucose-containing culture medium supplemented with hEGF (human epithelial growth factor) and bFGF (basic fibroblast growth factor) and comprising the usual inorganic salts, amino acids and vitamins necessary for the growth of mammalian cells and in particular wherein the mature hepatocytes are frozen in a serum-containing culture medium in the presence of a cryoprotecting agent and then thawed prior to culturing according to step (i).

The characterization of the human non-oval liver stem/progenitor cells disclosed in WO 2006/126236 and the method of preparing thereof are herein fully incorporated by reference.

The use of HLSCs in the present invention is preferred for a number of reasons: 1) they are relatively easy to isolate and expand, 2) they are characterized by a degree of proliferation that allows to provide a suitable number of cells for therapeutic use, 3) they can be used autologously and 4) they avoid ethical concerns. Furthermore, the liver and the pancreas share common embryonic origins and the developing liver has been shown to exhibit transcriptional features similar to the adult pancreas (Bose B et al. Cell Biol Int. 2012; 36(11): 1013-20). However, since it is envisaged that poly-cationic substances shall be effective in promoting aggregation and differentiation of other adult stem cells than HLSCs, the scope of the invention is not limited to the use of HLSCs only, but it includes the use of any adult stem cells type.

As mentioned above, the pancreatic islet-like cells structures obtained by the method of the present invention, are characterized by a unique combination of morphological and functional features which is not observed in other islet-like cells structures prepared by the methods of the prior art. Accordingly, the scope of the invention also includes a spheroid pancreatic islet-like cell structure as defined in the appended claims.

In particular, the spheroid pancreatic islet-like cell structure according to the present invention is advantageously characterized by a diameter of from 50 to 250 µm, preferably of from 50 to 200 µm, which is comparable to the naturally-occurring human pancreatic islets. It is also characterized by a volume, expressed as IEQ/100 ILS, ranging from 30 to 200 µm, preferably from 50 to 130 µM and, even more advantageously, by the ability to express, at the protein level, all of the pancreatic hormones which are usually expressed by human pancreatic islets, i.e. insulin, glucagon, pancreatic polypeptide, somatostatin and ghrelin.

Within the context of the present description, IEQ/100 ILS is the Islets Equivalent of an average diameter of 150 µm (IEQ) normalized to 100 islets (ILS). According to conventional protocols, the IEQ of islets isolated from the pancreas and used for transplantation is determined as follows. Suspended islets isolated from the pancreas are evaluated both in number and size (diameter) in order to determine the total islets equivalent (i.e. total islets volume). Islets diameter assessment takes into account 50 µm diameter range increments, from 50 µm to >350 µm, without taking into account diameters <50 µm, that do not provide a significant contribution to the total volume. A relative conversion factor is conventionally used to convert the total islets number to Islets Equivalent of an average diameter of 150 µm (IEQ).

Suspended islets isolated from the pancreas are separated in different layers based on their degree of purity. An islet sample from each layer of the final product is then analyzed: the total number of islets and the IEQ are then calculated based on the number, the purity and the size of the islets, using standardized methods. Since in the context of the present invention the islet-like structures are obtained from cultured cells, that are adherent to the plate, the inventors assessed both the number and the diameter of the islet-like structures by analyzing 200 10× micrographs, randomly selected, per experiment, and expressed the results as %±SD (FIG. 12 A) and IEQ normalized to 100 islets (FIG. 12 C).

Thanks to the above-illustrated features, the spheroid pancreatic islet-like cell structure according to the present invention are particularly suitable for use both in clinical application, such as in a method treatment of diabetes by pancreatic islet transplantation, and in in vitro applications, such as screening methods for identifying substances capable of promoting the expression of one or more pancreatic hormones by pancreatic islet cells or for identifying substances capable of exerting a cytotoxic effect on pancreatic islet cells.

The following examples disclose in detail the differentiation of HLSCs into spheroid pancreatic islet-like cell structures according to the present invention, using protamine as the poly-cationic substance. However, the examples are not intended to limit the purpose and scope of the invention.

EXAMPLES

1. HLSC Culture and Expansion
1.1 Isolation, Characterization and Culture of HLSCs HLSCs lines are isolated from healthy liver tissues of patients undergoing hepatectomies and characterized as previously described (Mohamad Buang M L et al. Arch Med Res. 2012; 43(1): 83-8). Specifically, HLSCs are seeded in 75 $cm^3$ culture flasks and cultured in a medium (see Table 1) containing a 3 to 1 proportion of α-minimum essential medium and endothelial cell basal medium-1, supplemented with L-glutamine 2 mM, penicillin 100 UI/ml/streptomycin 100 µg/ml and 10% Fetal Bovine Serum. Cells are maintained in a humidified 5% $CO_2$ incubator at 37° C.

1.2 Detachment of HLSCs

Once up to a ≈80% confluence, cells are washed twice with PBS and incubated with trypsin-EDTA 1× for about 5 minutes at 37° C., in order to induce cell detachment. Trypsin activity is subsequently neutralized by adding RPMI supplemented with L-glutamine 2 mM, penicillin 100 UI/ml/streptomycin 100 µg/ml and 10% Fetal Bovine Serum. Then, cells are harvested by centrifugation at 1200 rpm for 5 minutes, the supernatant is removed and the pellet re-suspended in culture medium and split among five 75 $cm^3$ culture flasks.

1.3 Cryopreservation of Cells

Cells up to a ≈80% confluence are detached and harvested by centrifugation as described in paragraph 1.2. The cells are counted and $10^6$ cells per vial are cryopreserved. The cell pellet is resuspended in a 1 ml solution containing 90% FBS and 10% dimethyl sulphoxide (DMSO) and placed into pre-cooled cryovial/s. The cryovials are frozen at −80° C. overnight before being placed into the liquid nitrogen container at −196° C.

1.4 Thawing of Cryopreserved Cells

A vial of frozen HLSCs is removed from the liquid nitrogen tank and placed in a beaker of water pre-warmed to 37° C. Once the cell suspension has completely thawed, it is placed into a sterile 50 ml falcon tube with 10 ml of sterile media and centrifuged at 1200 rpm for 5 minutes. The cell pellet is then resuspended in culture medium and split in three 75 $cm^3$ culture flask and left to attach overnight at 37° C. in a humidified 5% $CO_2$ incubator. The medium is changed the following day.

2. HLSC Differentiation into Islets-Like Structures.

HLSCs at a density of $12×10^3/cm^2$ are seeded in 25 $cm^3$ culture flasks or in a Petri dish 100×20 mm in the differentiation culture medium 1 (see Table 1) consisting in RPMI 1640 or DMEM supplemented with 10% Fetal Bovine Serum, glucose 11.6 mM, protamin chloride 10 µg/ml, L-glutamine 2 mM and penicillin 100 UI/ml/streptomycin 100 µg/ml. Cells are placed, for a period of 4 days, without changing the medium, in a humidified 5% $CO_2$ incubator at 37° C. On day 5, the medium is replaced with differentiation culture medium 2 (see Table 3) consisting in RPMI 1640 or DMEM supplemented with 10% FBS, glucose 11.6 mM, L-glutamine 2 mM and penicillin 100 UI/ml/streptomycin 100 µg/ml. Medium is subsequently changed every other day. Within 2 to 4 days cells are expected to start organizing in islets-like structures that reach a maximum number after 14-18 days (FIG. 1).

TABLE 1

HLSC culture medium

|  | Final concentration | Volume (ml) |
| --- | --- | --- |
| Final volume |  | 250 |
| α-MEM |  | 165 |
| EBM |  | 55 |
| FBS | 10% | 25 |
| Penicillin 10000 UI/ml/streptomycin 10 mg/ml | 100 UI/ml/100 ug/ml | 2.5 |
| Glutamine 200 mM | 2 mM | 2.5 |

TABLE 2

HLSC differentiation medium 1

|  | Final concentration | Volume (ml) |
| --- | --- | --- |
| Final volume |  | 250 |
| RPMI 1640 or DMEM |  | 216.85 |
| FBS | 10% | 25 |
| Penicillin/streptomycin | 100 UI/ml/100 ug/ml | 2.5 |
| Glutamine 200 mM | 2 mM | 2.5 |
| Glucose 1M | 11.6 mM | 2.9 |
| Protamine 10 mg/ml | 10 ug/ml | 0.25 |

TABLE 3

HLSC differentiation medium 2

|  | Final concentration | Volume (ml) |
| --- | --- | --- |
| Final volume |  | 250 |
| RPMI or DMEM |  | 217.1 |
| FBS | 10% | 25 |
| Penicillin/streptomycin | 100 UI/ml/100 ug/ml | 2.5 |
| Glutamine 200 mM | 2 mM | 2.5 |
| Glucose 1M | 11.6 mM | 2.9 |

The results obtained are illustrated in the appended drawings, the content of which is briefly illustrated herein below.

FIG. 1: representative 20×micrographs showing HLSCs in basal culture medium (FIG. 1A) and following culture in differentiation medium with protamine (FIG. 1B-FIG.1D). After 24 h, the cells changed in morphology and started forming small clusters (FIG. 1B) that progressively increased in both size and number, reaching a maximum number after a culture period of 18 days (FIG. 1C). (FIG. 1D) 40×micrograph showing islets-like structures after a culture period of 18 days. (FIG. 1E) Graph showing the total number of islets-like structures per 25 cm$^3$ culture flask after 18 days of culture. (FIG. 1F) Graph representing the mean±SD number of islets-like structures after 18 days of culture (n=10).

Figure 3:
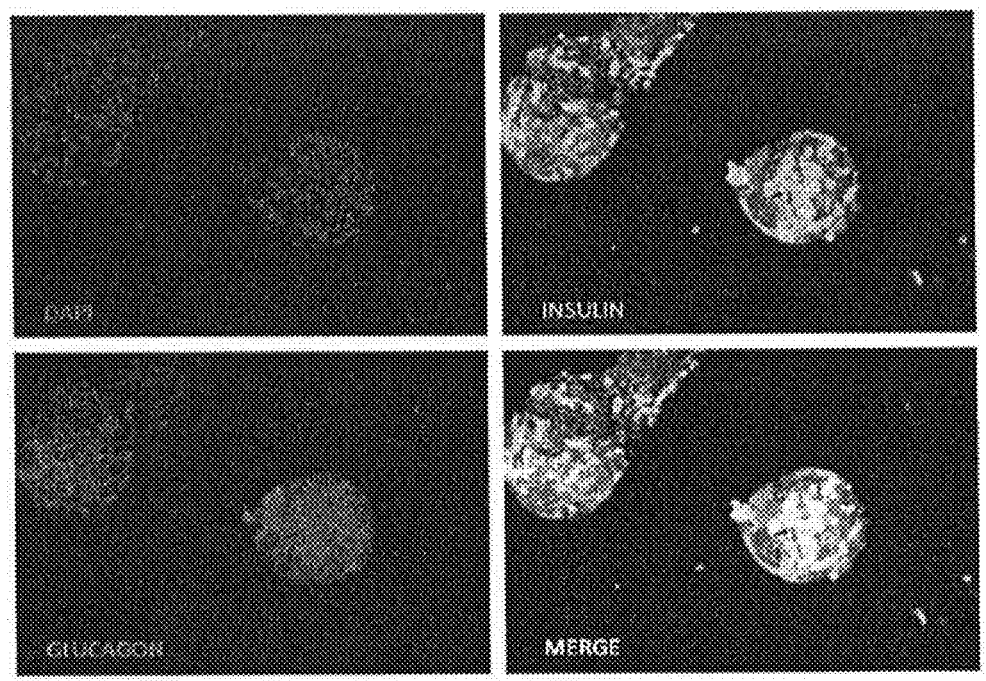
Figure 4:
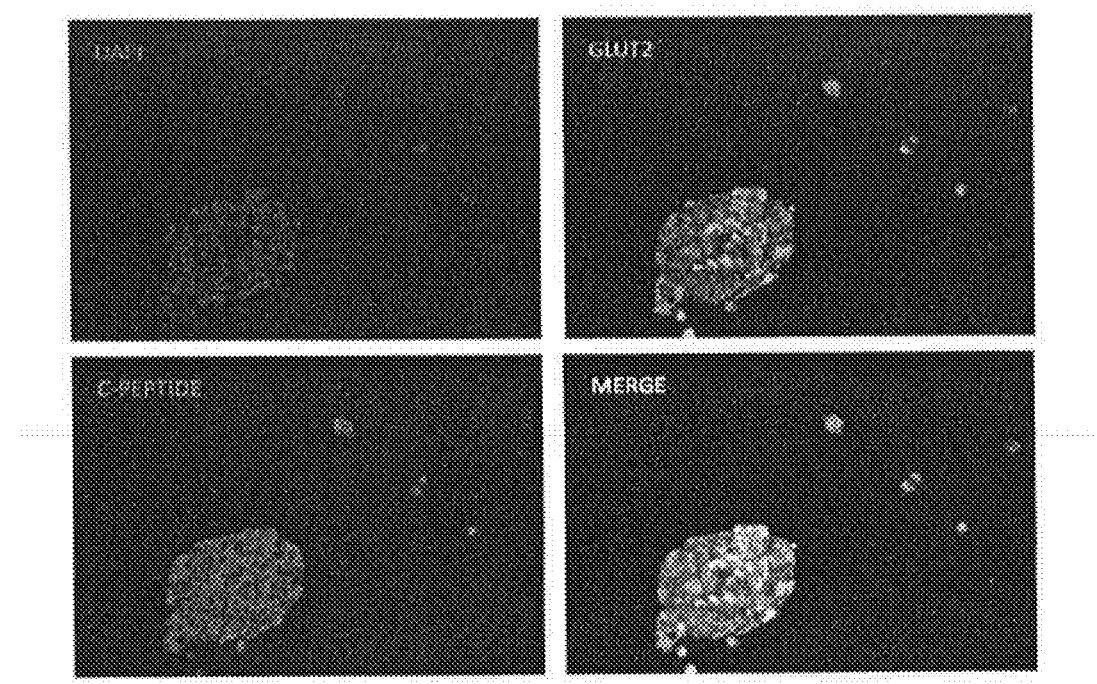
Figure 5:
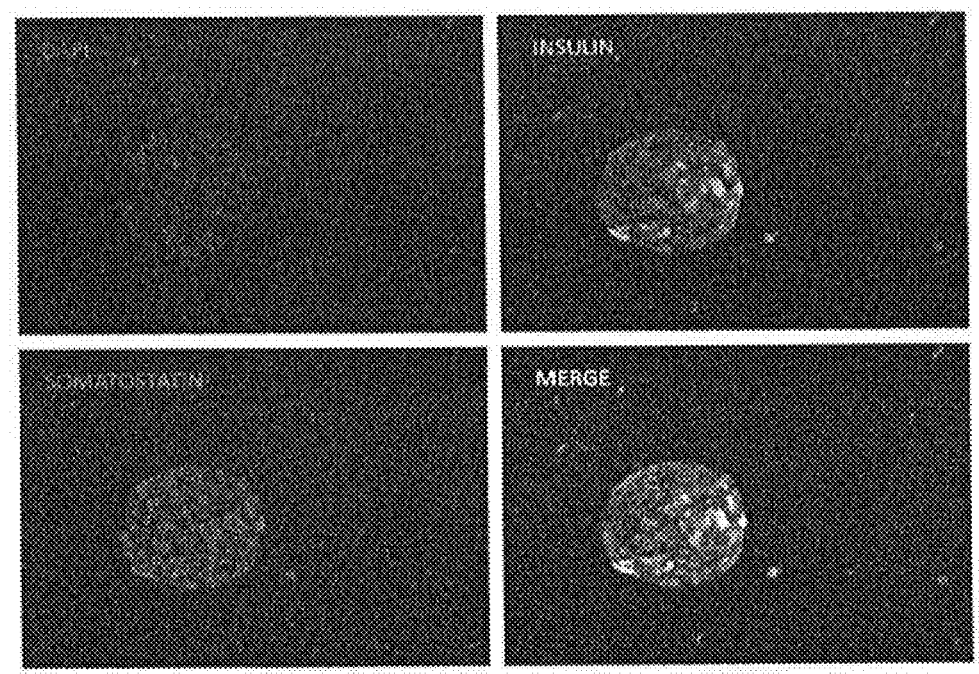
Figure 6:
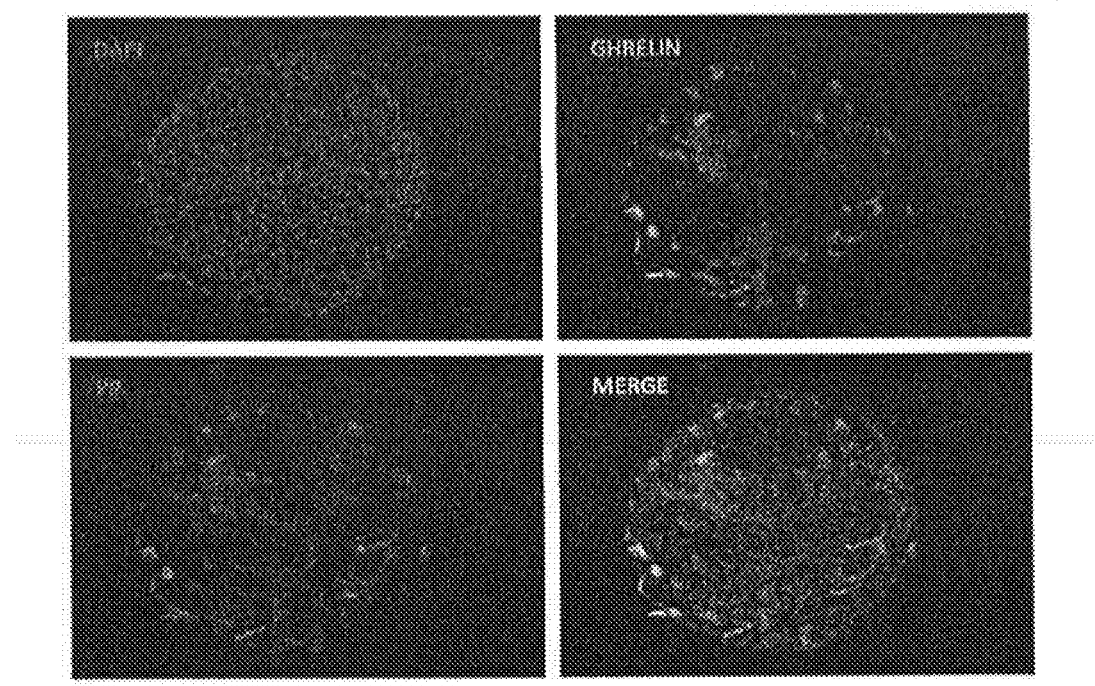
Figure 7:
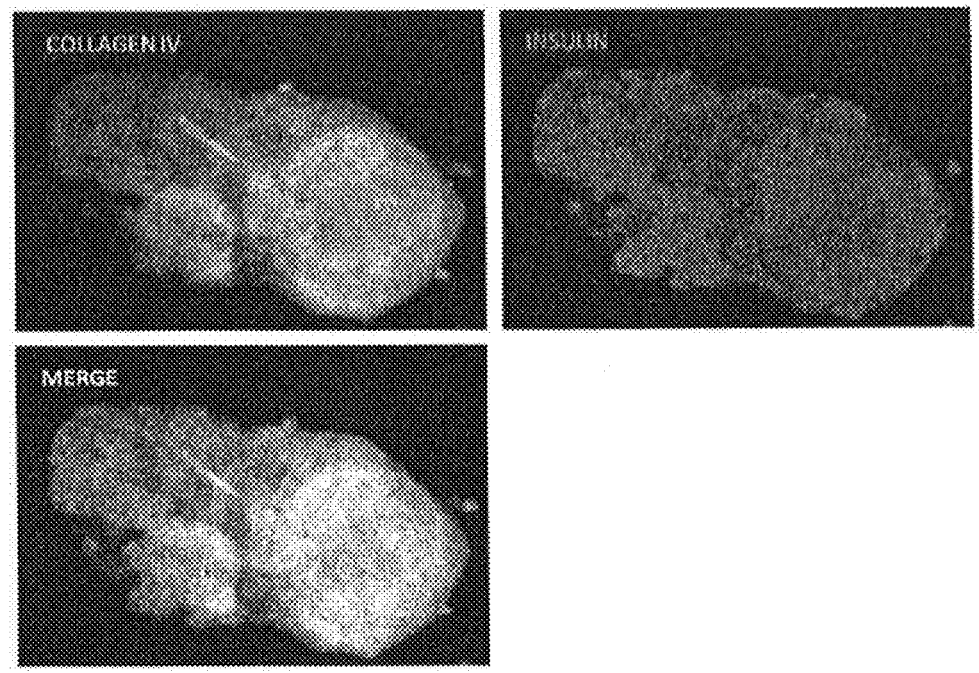
Figure 8:
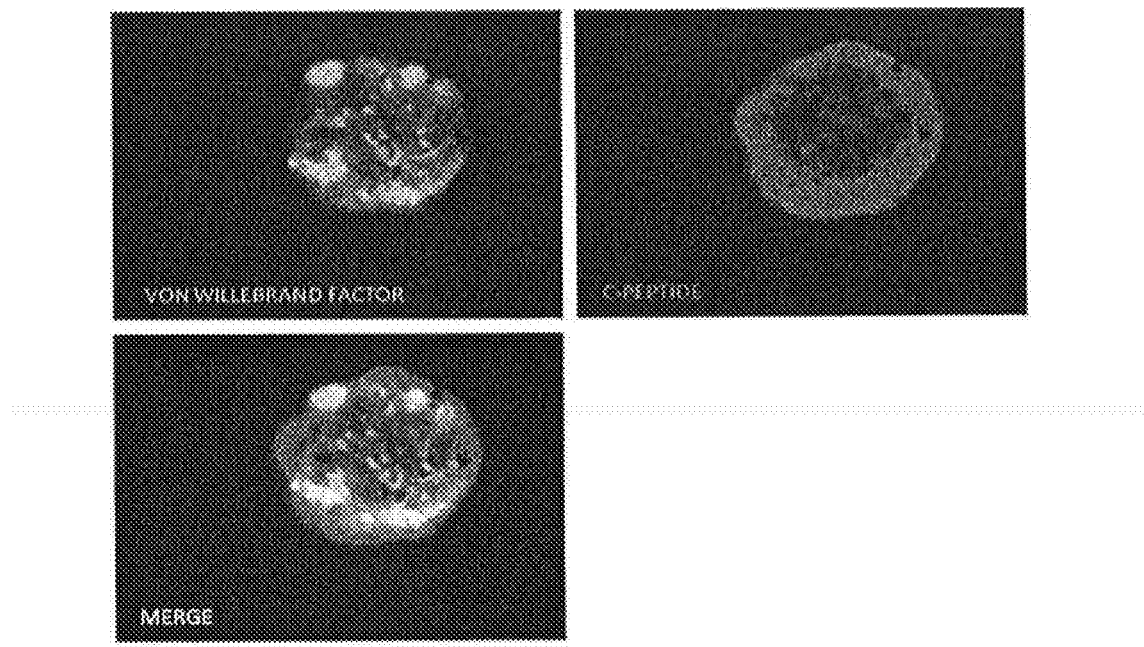

FIGS. 2-8: representative pictures showing islet-like structures characterization by immunofluorescence after 14 days of culture: islets-like structures become positively stained for both PDX-1 and NgN3 (FIG. 2), insulin and glucagon FIG. 3), C-peptide and GLUT-2 (FIG. 4), somatostatin (FIG. 5), ghrelin and PP (FIG. 6), collagen IV (FIG. 7) and von Willebrand Factor (FIG. 8).

Figure 9:
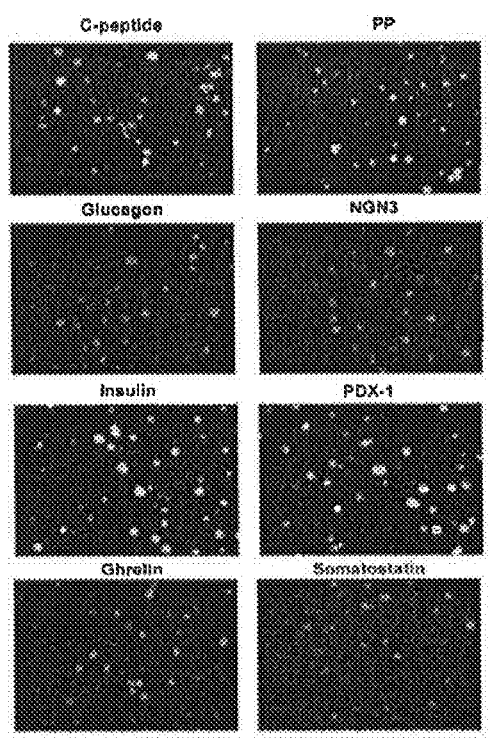
Figure 9:
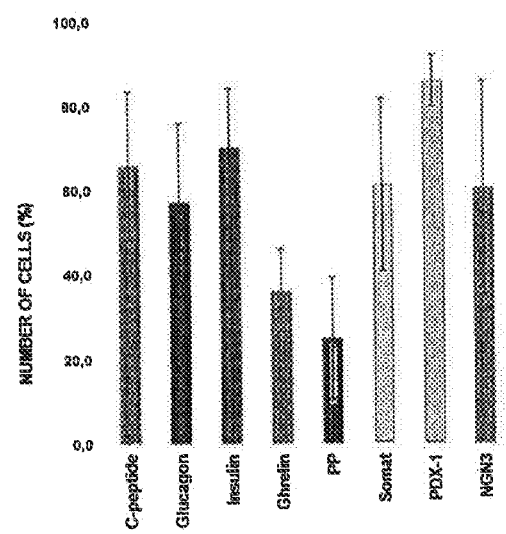

FIG. 9: representative pictures showing immunofluorescence characterization of islet-like structures cells following islet-like structures disaggregation (trypsin 1×) after 14 days of culture.

Figure 10:
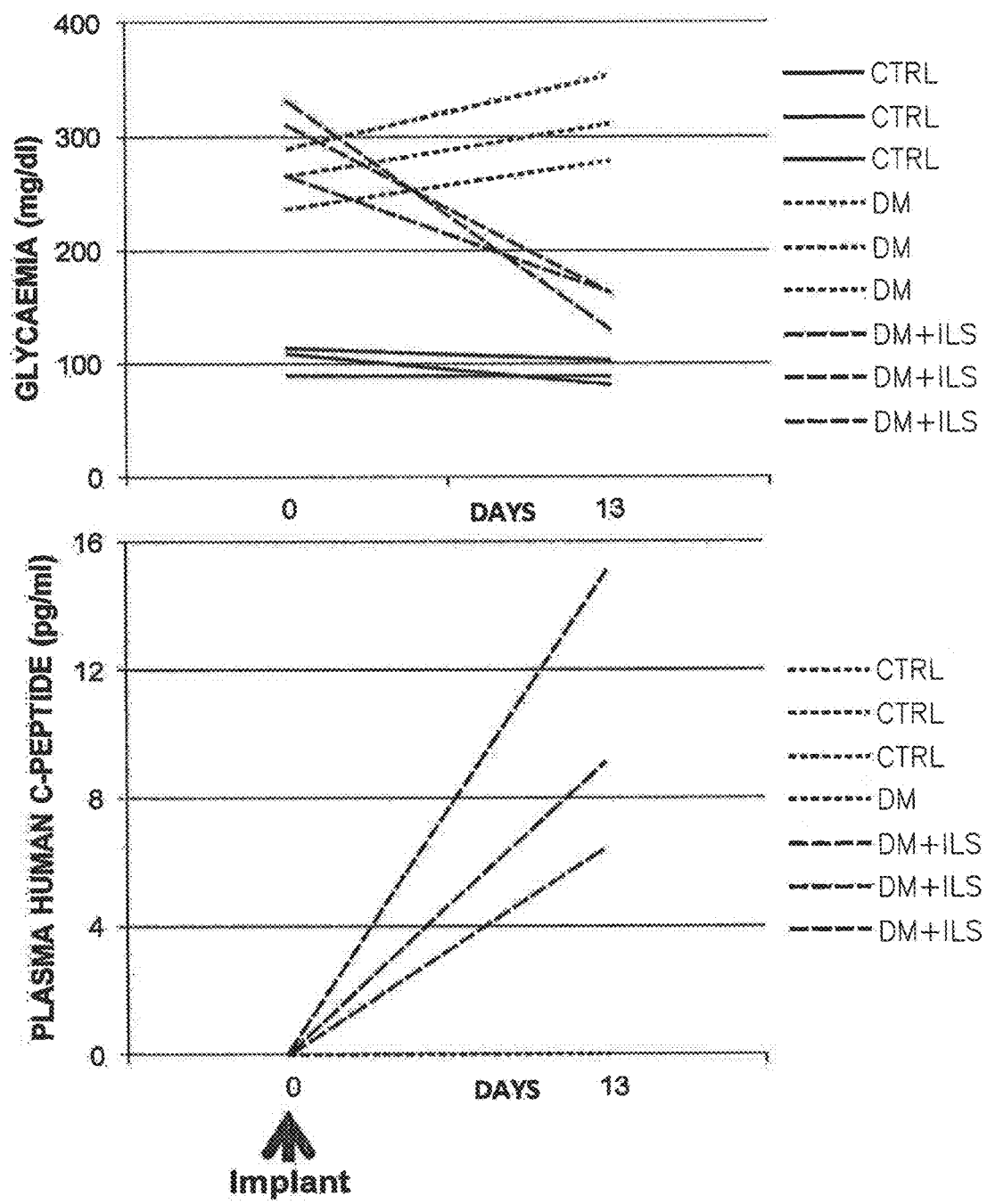

FIG. 10: graph showing both blood glucose and human C-peptide levels in non-diabetic SCID mice (solid line, CTRL), streptozotocin-induced (55 mg/kg/day for 5 days) diabetic SCID mice (dotted line, DM) and streptozotocin-induced diabetic SCID mice that received HLSC derived islets-like structures implant (5000 IEQ/kg) under the renal capsule (dashed line, DM+LS), before and 13 days following the implant. Compared to diabetic mice, diabetic mice that received islets-like structures implant had a significant decrease in blood glucose levels. This was paralleled by a concomitant increase in human C-peptide, that remained undetectable in both non diabetic SOD mice and in diabetic SCID mice that did not receive the implant, FIG. 11: graph showing islets-like structure (11LS) formation following HLSCs culture in RPMI or DMEM based medium supplemented with FBS 10% (F), FBS 10%+glucose 11.6 mM (FG) or FBS 10%+glucose 11.6 mM+protamine chloride 10 µg/ml(FGP) for 48 hours.

Figure 12A:
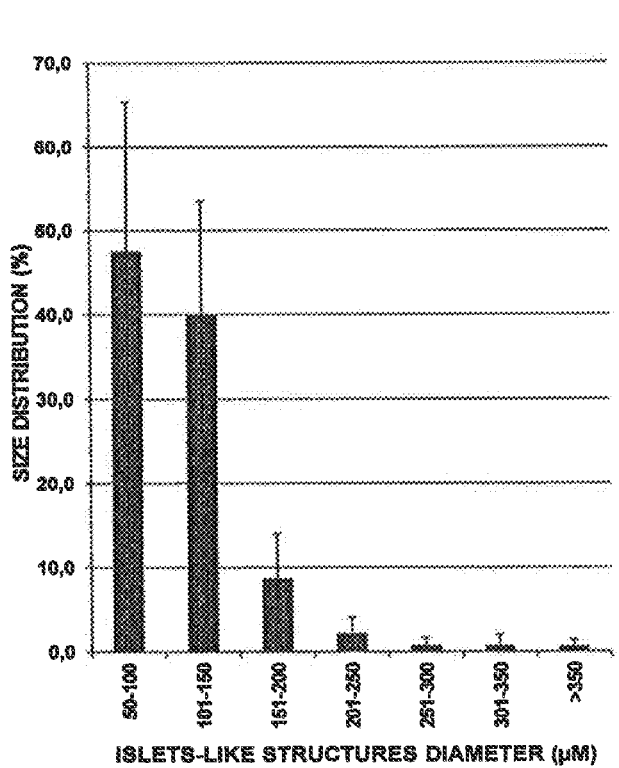
Figure 12B:
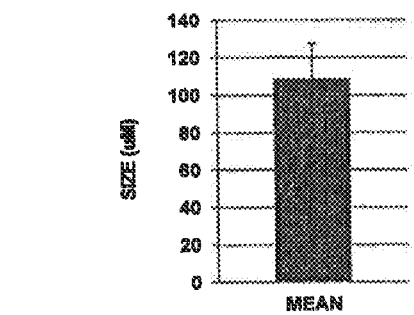
Figure 12C:
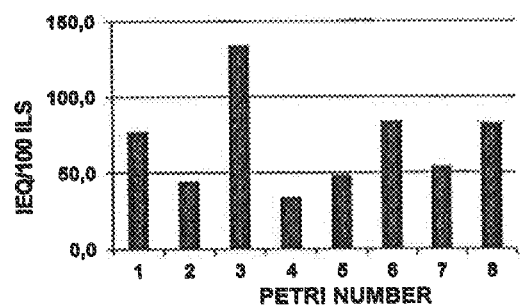

FIG. 12: graphs showing the size distribution (FIG. 12A), the mean±SD diameter (FIG. 12B) and IEQ/100 ILS (FIG. 12C) of islets-like structures derived from HLSCs following 14 days of culture in RPMI based medium supplemented with FBS 10%+glucose 11.6 mM+protamine chloride 10 µg/ml, FIG. 13: Glucose does not affect islets-like structures (ILS) formation (FIG. 13A), but plays a key role in inducing endocrine specification and insulin/glucagon expression (FIG. 13B). A, Representative picture and graph showing islets-like structure formation following culture (4 days) in RPMI/DMEM supplemented with protamine chloride 10 µg/ml (F) without or with different glucose concentrations (6, 11.6 and 28 mM). FIG. 13B. Representative picture showing PDX-1, NgN3, insulin and glucagon expression in RPMI-based medium with glucose 1 or 25 mM.

Figure 14:
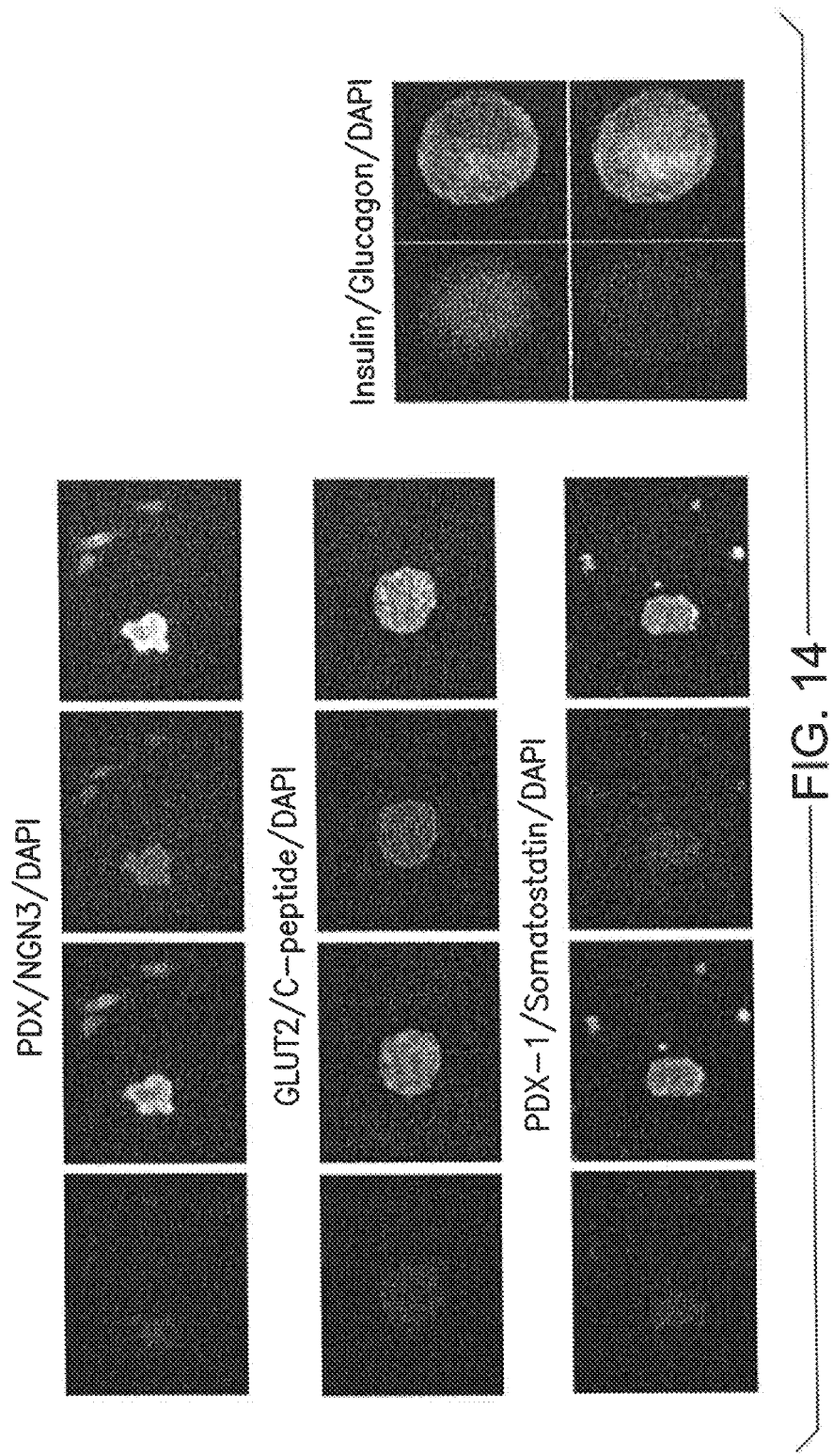

FIG. 14: representative pictures showing the expression of PDX-1, NgN3, GLUT-2, C-peptide, glucagon and somatostatin in cells cultivated in a poly-lysine differentiation medium.

The invention claimed is:

1. An artificially grown spheroid pancreatic islet-like cell structure having a diameter of from 50 to 250 µm and comprising differentiated cells derived from a human liver stem cell (HLSC) and expressing the pancreatic hormones insulin, glucagon, pancreatic polypeptide, somatostatin, and ghrelin and the markers PDX-1 and NgN3.

2. The artificially grown spheroid pancreatic islet-like cell structure according to claim 1, which has a diameter of from 50 to 200 µm.

3. The artificially grown spheroid pancreatic islet-like cell structure according to claim 1, wherein the differentiated cells further express the markers selected from the group consisting of C-peptide, Glut-2, collagen IV, and Von Willebrand factor and a combination thereof.

* * * * *